(12) United States Patent
Li et al.

(10) Patent No.: US 8,399,237 B2
(45) Date of Patent: Mar. 19, 2013

(54) PSEUDOMONAS ALCALIPHILA MBR AND ITS APPLICATION IN BIOREDUCTION AND BIOSORPTION

(75) Inventors: Daping Li, Sichuan (CN); Xiaohong He, Sichuan (CN); Yong Tao, Sichuan (CN); Xiaomei Wang, Sichuan (CN)

(73) Assignee: Chengdu Institute of Biology, Chinese Academy of Sciences, Chengdu (CN)

( * ) Notice: Subject to any disclaimer, the term of this patent is extended or adjusted under 35 U.S.C. 154(b) by 47 days.

(21) Appl. No.: 12/921,780

(22) PCT Filed: Mar. 12, 2009

(86) PCT No.: PCT/CN2009/070709
§ 371 (c)(1),
(2), (4) Date: Sep. 9, 2010

(87) PCT Pub. No.: WO2009/111974
PCT Pub. Date: Sep. 17, 2009

(65) Prior Publication Data
US 2011/0269169 A1  Nov. 3, 2011

(30) Foreign Application Priority Data
Mar. 12, 2008 (CN) .......................... 2008 1 0044958

(51) Int. Cl.
*C12N 1/00* (2006.01)
*C12N 1/22* (2006.01)
(52) U.S. Cl. .................................. 435/243; 435/252.34
(58) Field of Classification Search .................. 435/243, 435/252.34
See application file for complete search history.

(56) References Cited

U.S. PATENT DOCUMENTS
4,826,602 A   5/1989  Revis et al.

FOREIGN PATENT DOCUMENTS
CN        1683518 A    10/2005
CN      101016524 A     8/2007

OTHER PUBLICATIONS

Wang Jinyu et al., "A strain of *Pseudomonas* fluorescens with multi-paths of nitrogen metabolism," Acta Pedologica Sinica, vol. 44, No. 1, pp. 144-149, Jan. 31, 2007.
Yumoto, Isao et al., "*Pseudomonas alcaliphila* sp. nov., a novel facultatively Psychrophilic alkallphile Isolated from seawater", International Journal of Systematic and Evolutionary Microbiology, vol. 51, p. 349-355,31, (Dec. 2001).

*Primary Examiner* — Karen Cochrane Carlson
*Assistant Examiner* — Natalie Moss
(74) *Attorney, Agent, or Firm* — Birch, Stewart, Kolasch & Birch, LLP

(57) ABSTRACT

The present invention relates to microbiology technology field. More particularly, it relates to *Pseudomonas alcaliphila* MBR CGMCC 2318 which has the ability to reduce and adsorb metal and nonmetal ions. It also relates to methods of bioreduction and biosorption using the said strain by means of its property of reducing nitrate to ammonium and adsorbing metal ions to reduce the metal and nonmetal ions in the solution to elementary state under aerobic conditions. The present invention also relates to application of the said strain in bio-metallurgy, production of metal and nonmetal elementary substance, treatment of wastewater containing metal ions, and removal of harmful metal and nonmetal ions contained in soil and water. The strain of the present invention is easy to cultivate. The method of bioreduction and biosorption by it is very simple and can be widely used in metallurgy, treatment of wastewater and removal of harmful substances in soil and water.

20 Claims, 6 Drawing Sheets

PSEUDOMONAS ALCALIPHILA MBR AND ITS APPLICATION IN BIOREDUCTION AND BIOSORPTION

This Application is the National Phase Under 35 U.S.C. §371 of PCT International Application No. PCT/CN2009/070709 which had an International filing date of Mar. 12, 2009, which claims priority to Chinese Patent Application No. 200810044958.5 filed on Mar. 12, 2008. The entire contents of all applications listed above are hereby incorporated by reference.

The present application claims the priority of the Chinese patent application CN200810044958.5 entitled "*Pseudomonas alcaliphila* MBR and its application in bioreduction and biosorption" submitted on Mar. 12, 2008.

FIELD OF INVENTION

The present invention relates to the microbiology technology field. More particularly, it relates to a *Pseudomonas alcaliphila* MBR, the methods of bioreduction and biosorption using it, and the application of the strain described.

BACKGROUND OF THE INVENTION

Dissimilatory reduction of metal and nonmetal elements is a process in which metal and nonmetal elements are reduced as the terminal electron acceptor during microbial respiration. The research on the dissimilatory reduction of metal and nonmetal elements has received great attention from scholars in various countries. This dissimilatory reduction can not only reduce or eliminate harm to human being's health brought by toxic metal and nonmetal ions in the environment and effectively recover all kinds of precious metals in polymetallic ores and tailings, but also produce nanomaterials and catalysts via artificial approach. The study on the bio-reduction of selenium, tellurium and other non-metal elements has become a hot spot in the international material field.

The study on the metal dissimilatory reduction traces back to using microorganisms to reduce Fe (III) and Mn (IV). It has been found that microorganisms can utilize organic acids or hydrogen as electron donor to reduce Fe (III) and Mn (IV) to Fe (II) and Mn (II) respectively. In the past decade, scholars have also discovered that chromium (VI), Vanadium (V), Cobalt (III), Palladium (II), Rhodium (III), Europium (III) and some radioactive elements, such as Uranium (VI), Plutonium (VI), Neptunium (V), Technetium (VII), and other high-valence ions or oxides, which act as electron donors, can be reduced to the low-valence ions or oxides by microorganisms oxidizing organic acids or hydrogen. In addition, some ions such as Palladium, Mercury, Rhodium and Europium can be directly reduced to elementary substances by microorganisms.

In the existing published patent literature, two U.S. patents (U.S. Pat. No. 5,569,596 and U.S. Pat. No. 5,739,028) respectively describe a chromium (VI) resistant strain *Shewanella alga* reducing chromium (VI) to form insoluble chromium (III) sediment under anaerobic conditions and a method of removing the sediment from pollutants. A Chinese patent (patent number: CN93106616.6) describes strains of anaerobic bacteria such as *Fusobacterium nucleatum* reducing chromium (VI) to generate insoluble chromium (III) precipitation, and the usage to remove chromium from some heavy metal wastewater such as electroplating wastewater. Two U.S. patents (U.S. Pat. No. 5,055,130 and U.S. Pat. No. 5,283,192) describe a strain of *Bacillus polymyxa* treating the silver manganese mine and a method of promoting recovery of manganese and silver by reducing of Mn (IV) oxide to soluble Mn (II) ions. Moreover, a U.S. patent (U.S. Pat. No. 6,218,171) reports the method of non-growing cells of two *Shewanelia* bacteria (*Shewanelia putrifacians* and *Shewanelia alga*) reducing the radioactive element Tc (VII) to Tc (IV) under the anaerobic conditions. In addition, there are two U.S. patents (U.S. Pat. No. 5,352,608 and U.S. Pat. No. 5,804,424) which respectively cover a photosynthetic bacteria (*Rhodobacter sphaeroides*) reducing the rhodium (III) and Eu (III) oxide into elementary substances under anaerobic conditions and depositing on the cell membrane. Lastly, a Chinese patent (patent No. ZL 99815312.5) describes some reducing bacteria such as *Desulfovibrio* sp., *Pseudomonas* sp., *Shewanella* sp., which are used in heavy metal wastewater treatment and reduce iron (III) and manganese (IV) to their low state, respectively.

In addition to patent documents, there are many articles which report the research of the microbial reduction of metals, most of which focus on the earliest discovery of bioreduction of iron (III) and manganese (IV). D. R. Lovely who has made an outstanding contribution in this field, published three articles about the biological reduction of iron (III) in Nature (Anaerobic production of magnetite by a dissimilatory iron-reducing microorganism, Nature, 330, 252-254, (1987); Oxidation of aromatic contaminants coupled to microbial iron reduction, Nature, 339, 298-300, (1989); *Geobacter metallireducens* accesses insoluble Fe(III) oxide by chemotaxis, Nature, 416, 767-769, (2002)). Moreover, many articles relate to the application of *Shewanella* sp. and *Geobacter* sp. in the field of metal reduction. Chromium (VI) is a hazardous substance in the environment, whose biological reduction has also been paid attention by scholars. More literature reports the sulfate-reducing bacteria on Cr (VI) reduction and the formation of insoluble chromium (III) compounds, including literature written by some Chinese scholars such as Fude Li and Jidong Gu (Ji-Dong Gu, International Biodeterioration & Biodegradation, 59, 8-15, (2007); Fude Li et al., Study on Reduction of Hexavalent Chromium(VI) by Sulfate-reducing Bacteria, 1993, Environmental Science, 14(6): 1-4). Hillol and Sarah reported the chromium (VI) reduction by the *Shewanella alga* and *Shewanella oneidensis* MR-1, respectively (Sarah S. Middleton, et al., Cometabolism of Cr(VI) by *Shewanella oneidensis* MR-1 Produces Cell-Associated Reduced Chromium and Inhibits Growth. Biotechnology and Bioengineering 83(6), 627-637, (2003). Hillol Guha, Biogeochemical influence on transport of chromium in manganese sediments: experimental and modeling approaches, Journal of Contaminant Hydrology, 70, 1-36, (2004)). Furthermore, Vanadium (V) as a high-valence metal has been more studied in recent years. Researchers have found that such bacteria as *Geobacter* sp., *Shewanella* sp. and *Pseudomonas* sp. have the ability of reducing vanadium (V) to the insoluble vanadium (IV) compounds (Judith M. Myers et al., Vanadium (V) Reduction by *Shewanella oneidensis* MR-1 Requires Menaquinone and Cytochromes from the Cytoplasmic and Outer Membranes, Appl. Environ. Microbial., 70(3), 1405-1412, (2004); Irene Ortiz-Bernad et al., Vanadium Respiration by *Geobacter metallireducens*: Novel Strategy for In Situ Removal of Vanadium from Groundwater. Appl. Environ. Microbial., 70(5), 3091-3095, (2004); A. N. Antipov et al., Vanadate Reduction by Molybdenum-Free Dissimilatory Nitrate Reductases from Vanadate-Reducing Bacteria. IUBMB Life, 50(1), 39-42, (2007)). Moreover, as for radioactive elements uranium (VI), because of its danger in the environment, biological reduction has become an important tool to eliminate the hazard. Two papers in Nature are both about the study on bioreduction of uranium (VI). As early as in 1991, D. R. Lovely published an article in Nature which reported that the use of iron (III)-reducing bacteria (*Alteromonas putrefaciens*) could reduce the U(VI) to insoluble uranium (IV) and the rate of reduction was significantly faster than that of non-biological reduction process. Some scholars have reported the research on the use of *Shewanella* sp. and *Geobacter* sp. to reduce other metal elements, which are high valence ions, such as Cobalt (III) (Caccavo Jr, F. et al., *Geobacter sulfurreducens* sp. nov., a hydrogen and acetate-oxidizing dissimilatory metal reducing microorganism, Appl. Environ. Microbiol. 60, 3752-3759, (1994)), Neptunium (V) (Lloyd, J. R., et al., Biological reduction and removal of pentavalent Np by the concerted action of two microorganisms, Environ. Sci. Technol. 34, 1297-1301, (2000)), Tc (VII) (Lloyd, J. R. and Macaskie, L. E. A novel phosphorImager based technique for monitoring the microbial reduction of technetium, Appl. Environ. Microbiol. 62, 578-582, (1996)), whose reduction products are low valence Cobalt (II), Neptunium (IV) and Tc (IV), respectively.

With the exception of the above metal elements, the bioreduction of some precious metals such as gold, silver, platinum, and palladium has been received a great attention by scholars. Some research results have been applied to precious metals smelting and processing of metal catalysts. Unlike other metal elements, owing to the inertia of the precious metal, most bioreduction products of them are elementary substances. Furthermore, microorganisms that participate in reduction show a biological diversity, among which sulfate-reducing bacteria, *Shewanella*, and *Bacillus, Pseudomonas, Enterobacteria, Corynebacterium* etc. are involved in the process of reduction. Chinese scholar YueYing Liu has done a large number of researches not only on reducing some precious metals ions such as gold, platinum, palladium to a simple substance, but also in the field of Palladium catalysts (Studies on Biosorption of Au($Au^{3+}$) by *Bacillus Megaterium* D01, Acta Microbiologica Sinica, 2000, 40(4):425-429). What's more, Wiatrowski H. A. uses *Shewanella* sp. and *Geobacter* sp. to reduce mercury (II) to mercury (0) directly through microbial reduction (Novel reduction of mercury (II) by mercury-sensitive dissimilatory metal reducing bacteria. Environ Sci Technol, 40(21), 6690-6, (2006)).

To sum up, with the exception of a small number of inert precious metal elements, the vast majority of metal elements in biological reduction are limited to transformation from high-valence to low and most completed under anaerobic conditions, while it is rare to be reported that metal ions are reduced directly into elementary state.

While from the standard electrode potential (in acid solution) in electrode reaction of the metal element, we can see that the precious metal elements gold (I), silver (I) and Pd (II) are reduced to their elementary substances with higher electrode potential, 1.68 (v), 0.80 (v) and 0.99 (v) respectively. In addition, the precious metal element platinum (IV) can be reduced by microorganism to the low valence platinum (II) or elemental platinum (0) by microorganism. The potential of two electrode of reduction reaction are 0.68 (v) and 0.73 (v) respectively. Apart from precious metals, mercury can be reduced to elementary substance by the microorganisms, and from the electrode potential, we can see that the electrode potential of Mercury (II) to reduce remains high, reaching 0.85 (v). As for the general metal elements such as iron (III), manganese (IV), chromium (VI), Vanadium (V), cobalt (III), uranium (VI) and plutonium (VI), when they are reduced from their high valence to the corresponding low state, i.e. iron (II), Mn (II), chromium (III), Vanadium (IV), cobalt (II), uranium (IV) and plutonium (IV), their electrode potential are 0.77(v), 1.23 (v), 1.33 (v), 1.00 (v), 1.82 (v), 0.62 (v) and 0.97(v), respectively.

The analysis of electrode potential of metal elements whose reduction involves microorganisms shows that the existing bioreduction process has a higher electrode potential, between 0.6 (v) and 1.8 (v). While metal elements with lower valence, such as iron (II), Mn (II), chromium (III), vanadium (II), Co (II), Uranium (III) and plutonium (IV) are further reduced to their zero valence substances, and their potentials in the electrode reaction are −0.44 (v), −1.18 (v), −0.74 (v), −1.18 (v), −0.28 (v), −1.8 (v) and −2.42 (v) respectively. So far, electrode reaction phenomenon of reducing such low electrode potential metal elements by microbes has not yet reported in the publications.

As far as the reduction of non-metal is concerned, the oxidation state of common non-metallic elements such as sulfate and nitrate are reduced to sulfide or nitrogen, nitrous oxide and other products by the sulfate-reducing bacteria or nitrate-reducing bacteria (denitrifying bacteria). In addition, in the area of sulfate reduction and nitrate reduction there has been too many literature and monographs published. As we know, a large number of microorganisms in the nature are involved in the biological reduction process of nitrogen oxide and sulfur oxide.

Moreover, the scholars have given enough attention to the biological reduction of some non-metallic elements such as arsenic, selenium and tellurium because of the health risks brought by an excess of them in the environment. Two U.S. patents (U.S. Pat. No. 5,352,608 and U.S. Pat. No. 5,804,424) describe under photosynthetic and heterotrophic conditions, two photosynthetic bacteria (*Rhodobacter sphaeroides* and *Rhodobacter capsulatus*) being able to reduce selenite and tellurite to their element (selenium and tellurium). Another two U.S. patents (U.S. Pat. No. 5,009,786 and U.S. Pat. No. 5,271,831) describe how to use microbial anoxic system to treat selenate wastewater, in which microorganisms are able to make use of organic acids and hydrogen as electron donor for the direct reduction of selenate, and the residual selenite can be reduced into single-selenium(0) by hydrogen sulfide created by microbes.

To date, there are a lot of reports relating to selenium and tellurium reduction. The early studies mainly concentrated on the resistance of microorganisms to selenium and tellurium. Since the mid-1990s, studies using photosynthetic bacteria to reduce tellurite and selenite to Te (0) and Se (0) have begun to be reported. V. Yurkov and A. Yamada respectively reported that photosynthetic bacteria (*Roseococcus thiosulfatophilus, Erythromicrobium ezovicum, Rhodobacter sphaeroides*) could reduce tellurite and selenite to Se (0) and Te (0) both under aerobic and anaerobic conditions. In addition, a Chinese scholar Dongliang Wang (Screening and identification of a photosynthetic bacterium reducing selenite to red elemental selenium, Acta Microbiologica Sinica, 2007, 47(1): 41-47) and Janine Kessi (Enzymic systems proposed to be involved in the dissimilatory reduction of selenite in the purple non-sulfur bacteria *Rhodospirillum rubrum* and *Rhodobacter capsulatus*. Microbiology, 152, 731-743, (2006)) separately reported the screening technology of a strain of selenite-reducing photosynthetic bacteria *Rhodobacter azotoformans* as well as the enzyme systems involved in the processes that *Rhodospirillum rubrum* and *Rhodobacter capsulatus* reduced selenite to Se (0). Besides photosynthetic bacteria, researchers also studied the reduction of selenite and tellurite based on the mechanisms of denitrifying bacteria reducing nitrate: Sridhar Viamajala investigated the reduction of selenitle when denitrifying bacteria were cultured in batch and reactor (Selenite reduction by a denitrifying culture: batch- and packed-bed reactor studies. Appl Microbiol Biotechnol, 71, 953-962, (2006)); MONIQUE SABATY et al. studied on the reduction of selenite and tellurite through the combination of periplasm and membrane of denitrifying bacteria with denitrifying enzyme (Characterization of the Reduction of Selenate and Tellurite by Nitrate Reductases., Appl. Environ. Microbial., 67(11), 5122-5126, (2001)); Michihiko Ike (Selenate Reduction By Bacteria Isolated From Aquatic Environment Free From Selenium Contamination. Wat. Res. 34(11), 3019-3025, (2000)) and J. M. Rajwade (Bioreduction of tellurite to elemental tellurium by Pseudomonasmendocina MCM B-180 and its practical application. Hydrometallurgy, 71, 243-248, (2003)) reduced selenate, selenite and tellurite to Se(0) and Te(0) with *Pseudomonas* spp (*Pseudomonas stutzeri, Pseudomonas uorescens* and *Pseudomonas mendocina*), respectively; Agnieszka Klonowska et al. studied the reduction of selenite and tellurate, utilizing metal-reducing bacteria under anaerobic conditions and found a large number of elemental selenium and tellurium precipitated outside the membrane in the form of nanoparticles; Chinese scholar Jidong Gu et al. (Chromate reduction by *Bacillus megaterium* TKW3 isolated from marine sediments, World Journal of Microbiology & Biotechnology, 21, 213-219, (2005)) and Ruiping Li et al. (Sodium selenite reduction to elemental selenium by *Bacillus* HBS4, Acta Petrologica Et Mineralogica, 598-603, 24(6), 2005) used *Bacillus* spp. to reduce selenite and also got elemental selenium. Studies on arsenic reduction are comparatively less. It has been found that arsenic (V) could be reduced to soluble but more toxic V(III) by SR-bacteria and pseudomonas under anaerobic conditions.

As a very important photoelectric conversion element, non-metal element silicon plays an important role in the field of solar cells and semiconductor materials as well as other photoelectric materials. However, we have not found any report about bio-reduction of silicon in the literature.

In conclusion, it seems that the study on the bio-reduction of rare nonmetal elements such as selenium and tellurium has been a hot point all over the world with the development of material science and made considerable progress, in addition to studies on the bio-reduction of conventional nonmetal elements such as nitrate and sulphate as well as their general application. As shown in the existing literature, elements mentioned above are the only ones that could be bio-reduced while there is no report concerning other elements found in the field of non-metal elements reduction.

The standard electrode potential of nonmetallic elements electrode reactions in acid solution shows that the electrode potentials are 0.96 (v) and 0.20 (v) respectively when nitrate and sulphate are reduced from high-valence (nitrogen(V), sulphur(VI)) to low-valence state (nitrogen (II), sulphur(IV)), while the electrode potentials of nitrogen (II) reduced through nitrogen (I) to nitrogen (0) are both higher (1.59 (v) and 1.77 (v), respectively), and, sulphur (IV) to sulphur(0) is 0.45 (v). From recent studies on bioreduction of selenium and tellurium, we can see that the electrode potentials of selenium and tellurium are 0.74 (v) and 0.56 (v) respectively when they are reduced from high-valence selenium (IV) and tellurium (IV)) to low valence (selenium (0) and tellurium (0)). Even that arsenic is reduced from arsenic (V) to arsenic (III), the electrode potential of arsenic can reach 0.56 (v).

Seeing from the above-mentioned elements, most of them can get a high potential (0.40v~1.77v) when they are reduced to simple substances, besides sulphur which is relatively low (0.20v) when it is reduced from sulphur (VI) to sulphur (IV). As for silicon (IV), the electrode potential of it can reach to −0.86 (v) when it is reduced to silicon (0), which may be the important reason for the high-valence silicon to be bio-reduced difficulty.

Treatment of heavy metal pollution has become an important environmental problem in recent years. Traditional methods to treat heavy metal pollution include chemical precipitation, electrolysis, ion exchange and physical adsorption etc. Biosorption has been a rapid-developing emerging heavy metal treatment technology in recent 10 years compared to those traditional methods. Biosorption is an effective approach to adsorb and recover metal ions by ion exchange, surface complexation, redox and electrostatic adsorption by using live or dead cells, which has advantages of high efficiency at low concentration, high adsorption capacity, selectivity, easy operation. Biosorption of heavy metals related research has been the focus of international environment field. Bacteria, alga, fungi, and some of their components have been successfully applied in removal of heavy metal ions from streams. Among these organisms, because of its high specific surface area, the bacteria caused widespread concern.

The important progress of biosorption firstly comes into the research of sulfate reducing bacteria and its application in biology treatment of heavy metal wastewater. Sulfate reducing bacteria and their metabolites (soluble sulfides) play an important role in the adsorption of metal ions, such as chromium, cadmium, nickel, zinc, and so on. Fude Li did an important contribution in this field, whose three published patents (patent Nos. CN93106616.6, CN96117479.X and WO9733837) refer to adsorption and reduction of heavy metals by sulfate reducing bacteria and other anaerobic bacteria and their application in electroplating wastewater and other wastewater containing metal ions. Besides sulfate reducing bacteria, scholars have also widely used bacteria, yeast, fungi and alga as the bio-adsorbent in recent years. For example, U.S. Pat. No. 5,055,402 proposed the use of dried dead alga to adsorb metal ions from wastewater. Moreover, U.S. Pat. No. 5,538,645 and U.S. Pat. No. 4,701,261 proposed adsorbing and recovering metal ions from wastewater by treated yeast. U.S. Pat. No. 4,690,894 proved that cells treated by lye could promote the adsorption effect of metal ions. A few patents raised the method that can improve metal ions adsorption using embedded microbial cells by hydrophilic material (U.S. Pat. No. 5,976,847 and CN02131031.9). Besides the patent literature above, a large number of general literatures refer to research of metal ions absorption of microbial cell.

Nevertheless, it is to be noted that these patents and general literatures mainly refer to non-growing cells of microbes that act the adsorbing material to adsorb metal ions, and the pretreatment of non-growing cells is complex, which limits adsorption efficiency. Meanwhile, literatures that relate to growing cells adsorbing metal ions are relative less.

Some microbes have the same adsorption function in their growing cells' metabolism. U.S. Pat. No. 6,383,388 describes a metal ion-resistant *Saccharomyces cerevisiae* which can adsorb and reduce chromium(VI) at low concentration (2 mg/L) to chromium(III) and adsorb such metal ions as molybdenum, nickel, zinc, calcium and cobalt in wastewater, in its growth. However, the patent did not mention the removal efficiency of other ions but that of chromium. U.S. Pat. No. 6,355,172, CN 1281524C and CN 1086366C proposed a technology of adsorbing metal ions by growing microbes attached on filter bed, in which wastewater continuously passes by filter bed, remove and wash off part of microbial cells in filter bed to recover metal ions adsorbed by the cells. By using microbes metabolism to form sulfides or metal oxides and hydroxides, the technology adopts a large amount of anaerobic microbes such as *Shewanella*, *Desulfovibrio* and *Desulfococcus* to deposit and recover metal ions. However, the patent did not mention the removal efficiency of metal ions.

Besides the electroplating industry, which is suitable for external biosorbent and removal of metal ions in anaerobic or anoxic environment because of its high concentration of metal ions in wastewater and little water, there are lots of other industries whose anaerobic conditions is difficult to control because of its varieties of metal ions, low concentration and large amount of water. Therefore, the biosorption under anaerobic condition is particularly important.

DETAILED DESCRIPTION OF THE INVENTION

Technical Question to be Solved

One object of the present invention is to provide a strain of *Pseudomonas alcaliphila* MBR (strain CGMCC No. 2318). The bacterium can produce ammonium through nitrate reduction, but also be able to reduce metal and non-metal ions in solution to simple substances, under aerobic conditions.

Another object of the present invention is to provide the application of the *Pseudomonas alcaliphila* MBR CGMCC2318 in reducing metal ions in solution, such as Fe(III), Mn(II), Cu(II), Ni(II), Cd(II), Co(II), Mo(VI), Pb(II) and Ti(IV), to elemental metals. Besides, the bacterium can also reduce non-metal ions including Si (IV), Se (IV) and Te (IV) to their elementary state, thus remove the harmful Se (IV) and Te (IV) of non-metal ions from water, soil and waste. The elemental production of bio-reduction, such as silicon, selenium and tellurium, find their use in semiconductor, photovoltaic materials, as well as food additives.

Another purpose of the present invention is the application of *Pseudomonas alcaliphila* MBR CGMCC2318 in removing metal ions such as Cu(II), Zn(II), Ni(II), Cd(II), Fe(III), Mn(II), Co(II), Pb(II) and Al(III) in solution at low concentration by using live cells to adsorb these metal ions.

Technical Plan

The bio-reducing bacterium provided by the present invention is a strain of *Pseudomonas alcaliphila* MBR, which has been preserved on Jan. 2, 2008 in China General Microbiological Culture Collection Center (CGMCC) of China Committee For Culture Collection of Microorganisms(CCCCM) (address: Datun Road, Chaoyang District, Beijing), and the Collection No. is CGMCC No. 2318.

*Pseudomonas alcaliphila* MBR CGMCC2318 has the characteristics of white colony with irregular colony edge but smooth, moist, shiny and sticky opaque. Scanning electron micrograph of the strain is shown in FIG. 1. After the morphological, physiological and biochemical characteristics and 16S rRNA gene sequence homology analysis, this strain is identified as *Pseudomonas alcaliphila*, whose physiological and biochemical characteristics are shown in Table 1. Its 16S rRNA gene sequence has been submitted to the NCBI databases (Accession No: EU307111) of the United States. The results of homology analysis are shown in table 2.

TABLE 1

The physiological and biochemical characteristics of *Pseudomonas alcaliphila* MBR CGMCC2318

| Physiological & bio-chemical indexes | Results | Physiological & biochemical indexes | Results |
| --- | --- | --- | --- |
| Gram stain | − | Xylose utilization | − |
| Endospore | None | $H_2S$ production | + |
| Oxygen utilization | Facultative anaerobic | Lipase | + |
| Motility | − | V.P test | + |
| Oxidase | + | Indole production | + |
| Contact enzyme | + | Gelatin liquefaction | + |
| Ethanol oxidation | − | Glucose fermentation | Oxidizing type |
| Acetate oxidation | − | Phenylalanine Dehydrogenase | − |
| Amylohydrolysis | − | Nitrate reduction | + |
| 5% NaCl | + | Growing in pH 6.0 | + |
| 10% NaCl | − | Growing in pH 9.0 | + |
| Citric acid utilization | + | Growing in 42° C. | + |

TABLE 2

Analysis of 16S rRNA gene sequence homology of *Pseudomonas alcaliphila* MBR CGMCC2318

| Strains | Accession No. | Identity |
| --- | --- | --- |
| *Pseudomonas alcaliphila* (T); AL15-21. | AB030583 | 99.6% |
| *Pseudomonas* cf. *pseudoalcaligenes*; 3. | AF181570 | 99.7% |
| *Pseudomonas mendocina*; PC6. | DQ178222 | 99.7% |
| *Pseudomonas mendocina*; PC7. | DQ178223 | 99.7% |
| *Pseudomonas* sp. LOB-2. | DQ412061 | 99.7% |
| *Pseudomonas* sp. I91-7. | DQ192041 | 99.6% |
| *Pseudomonas* sp. 101-5. | DQ192044 | 99.6% |
| *Pseudomonas* sp. GW9. | EF550159 | 99.7% |
| *Pseudomonas* sp. P14. | EF627998 | 99.7% |
| *Pseudomonas alcaliphila*; D11. | EU082832 | 99.8% |
| *Pseudomonas* sp. SWS3-camc. | EF151237 | 99.7% |
| *Pseudomonas* sp. NF-2. | EU180220 | 99.6% |

The 16S rRNA gene sequences of *Pseudomonas alcaliphila* MBR CGMCC2318

```
TTTAGCGGCG GAAGGGTGAG TAATGCCTAG GAATCTGCCT GGTAGTGGGG GATAACGTTC

CGAAAGGAAC GCTAATACCG CATACGTCCT ACGGGAGAAA GCAGGGGACC TTCGGGCCTT

GCGCTATCAG ATGAGCCTAG GTCGGATTAG CTAGTTGGTG AGGTAATGGC TCACCAAGGC

GACGATCCGT AACTGGTCTG AGAGGATGAT CAGTCACACT GGAACTGAGA CACGGTCCAG

ACTCCTACGG GAGGCAGCAG TGGGGAATAT TGGACAATGG GCGAAAGCCT GATCCAGCCA

TGCCGCGTGT GTGAAGAAGG TCTTCGGATT GTAAAGCACT TTAAGTTGGG AGGAAGGGCA
```

-continued

```
TTAACCTAAT ACGTTAGTGT TTTGACGTTA CCGACAGAAT AAGCACCGGC TAACTTCGTG

CCAGCAGCCG CGGTAATACG AAGGGTGCAA GCGTTAATCG GAATTACTGG GCGTAAAGCG

CGCGTAGGTG GTTCGTTAAG TTGGATGTGA AAGCCCCGGG CTCAACCTGG GAACTGCATC

CAAAACTGGC GAGCTAGAGT ACGGTAGAGG GTGGTGGAAT TTCCTGTGTA GCGGTGAAAT

GCGTAGATAT AGGAAGGAAC ACCAGTGGCG AAGGCGACCA CCTGGACTGA TACTGACACT

GAGGTGCGAA AGCGTGGGGA GCAAACAGGA TTAGATACCC TGGTAGTCCA CGCCGTAAAC

GATGTCAACT AGCCGTTGGG TTCCTTGAGA ACTTAGTGGC GCAGCTAACG CATTAAGTTG

ACCGCCTGGG GAGTACGGCC GCAAGGTTAA AACTCAAATG AATTGACGGG GGCCCGCACA

AGCGGTGGAG CATGTGGTTT AATTCGAAGC AACGCGAAGA ACCTTACCTG GCCTTGACAT

GCTGAGAACT TTCCAGAGAT GGATTGGTGC CTTCGGGAGC TCAGACACAG GTGCTGCATG

GCTGTCGTCA GCTCGTGTCG TGAGATGTTG GGTTAAGTCC CGTAACGAGC GCAACCCTTG

TCCTTAGTTA CCAGCACGTA ATGGTGGGCA CTCTAAGGAG ACTGCCGGTG ACAAACCGGA

GGAAGGTGGG GATGACGTCA AGTCATCATG GCCCTTACGG CCAGGGCTAC ACACGTGCTA

CAATGGTCGG TACAAAGGGT TGCCAAGCCG CGAGGTGGAG CTAATCCCAT AAAACCGATC

GTAGTCCGGA TCGCAGTCTG CAACTCGACT GCGTGAAGTC GGAATCGCTA GTAATCGTGA

ATCAGAATGT CACGGTGAAT ACGTTCCCGG GCCTTGTACA CACCGCCCGT CACCCCATGG

GTGTGGGT
```

Medium (NCTS) of *Pseudomonas alcaliphila* MBR CGMCC2318 of the present invention consists of 0.5-1.0 g of $KNO_3$, 0.1-1.0 g of $KH_2PO_4$, 0.01-1.0 g of $MgSO_4.7H_2O$, 0.05 g of $FeCl_3.6H_2O$, 0.2 g of $CaCl_2.2H_2O$, 0.9-6.9 g of sodium citrate and 1000 mL of distilled water.

Screening, acclimation and features of *Pseudomonas alcaliphila* MBR of the present invention:

(1) Enrichment and Screening of Strain

The strain *Pseudomonas alcaliphila* MBR CGMCC2318 is isolated from the landfill leachate in Chengdu solid-waste disposal site. The medium for enrichment is as follows:

Solution A: 1.0 g of $KNO_3$, 5.0 ml of solution of 1% BTB (Bromothymol Blue) in alcohol, 500 ml of distilled water;

Solution B: 8.5 g of sodium citrate, 1.0 g of $KH_2PO_4$, 1.0 g of $MgSO_4.7H_2O$, 0.05 g of $FeCl_3.6H_2O$, 0.2 g of $CaCl_2.2H_2O$, 500 mL of distilled water.

Mix solution A and B, then adjust pH to 7.0, and sterilize at 115° C. for 15 min. After ten days of enrichment and culture, by the volume of the fresh medium (NCTS), the said landfill leachate is transferred by 1 vol % of inoculums to the fresh medium, and cultivated at 28° C. and 140 rpm. During the culture, detect qualitatively ammoniacal nitrogen in the culture solution, and then isolate several pure strains according to conventional microorganism's separation and purification method.

Inoculate several pure bacteria thus obtained in NCTS liquid medium respectively, and incubate at constant temperature 28° C. and 140 rpm under aerobic conditions. After detected by the same method as the above qualitative detection, a bacterium MBR with high efficiency of nitrate reduction is obtained. By the same physiological and biochemical characteristics and molecular identification, the present bacterium is identified as *Pseudomonas alcaliphila* MBR CGMCC2318.

(2) Performance of Reducing Nitrate to Ammonium

*Pseudomonas alcaliphila* MBR CGMCC2318 of the present invention can live on Giltay agar plate with nitrate as nitrogen source and sodium citrate as carbon sources for growth, thus reduce nitrate to ammonium. At 4° C., the culture medium having been fermented for 48 h is placed for 7 d, and then observe the needle-like crystals. Separately drop Nessler's reagent, Griess reagent and diphenylamine on the crystal and determine the ammonium contained in the crystal by the color change of the crystal. With sodium citrate as the electron donor and nitrate as the electron acceptor, the reduction of nitrogen is achieved.

(3) Reduction Feature of *Pseudomonas alcaliphila* MBR CGMCC2318

Strong metal reduction feature of *Pseudomonas alcaliphila* MBR CGMCC2318 is observed in the process of heavy metals adsorption. *Pseudomonas alcaliphila* MBR CGMCC2318 can use sodium citrate as electron donor to reduce some metal ions, including Fe (III), Mn(II), Cu(II), Ni(II), Cd(II), Co(II), Mo(VI), Pb(II), Ti(IV), and so on. The results of concentration determination for these metal ions show that *Pseudomonas alcaliphila* MBR CGMCC2318 has good reducibility at the metal ions concentration of 0.5-10 mM.

In addition, *Pseudomonas alcaliphila* MBR CGMCC2318 can also reduce Si (IV), Se (IV), Te (IV) to simple substances.

The procedures and method of reducing metal ions in the bio-reduction process of the present invention are shown as follows:

1. Inoculate the present strain MBR preserved on slant in 100 ml of sterilized LB liquid medium (10 g of tryptone, 5 g of yeast extract, 10 g of NaCl, 1000 ml of distilled water). Incubate at 28° C. and 110 rpm on shaking table for 3 d for activation, then by the volume of NCTS liquid medium, transfer 0.2 vol % of inoculum to the NCTS liquid medium. At 28° C., incubate for 48 h. Repeat the above process twice. The strain of *Pseudomonas alcaliphila* MBR CGMCC2318 thus obtained is ready for use.

2. 800 ml of said medium NCTS was equalized to eight triangular flasks (250 ml), with 100 ml for each. Stopple flasks with cotton plugs, and autoclave for 20 min at 121° C. After the medium cools, inoculate with 50-200 μl of *Pseudomonas alcaliphila* MBR CGMCC2318 from step 1.

3. Add one or more metallic salt(s) selected from $FeCl_3.6H_2O$, $MnSO_4.H_2O$, $CuSO_4.5H_2O$, $NiCl_2.6H_2O$, $3CdSO_4.8H_2O$, $CoCl_2.6H_2O$, $Na_2MoO_4.2H_2O$ and $Pb(NO_3)_2$ into the liquid mentioned in step 2, respectively. After incubating for 3-5 days with shaking table at pH6.0-10.0 28-38° C. and 100-150 rpm, centrifuge, wash with deionized water (repeating 2-3 times), centrifuge again, then recover the precipitate. After freeze-drying, detect the metal ions and elemental metals.

The titanium ion in the metal salt of $Ti(SO_4)_2$ can also be reduced to elemental titanium. However, since titanium sulfate can only dissolve in strong acid but not in water, titanium salts must be pretreated to form titanium chelate before the said reduction reaction. Particular procedures are as follows:

1. According to the weight ratio of 1:0.25-3, add 15-18 wt % of $Ti(SO_4)_2$ solution in 25-28 wt % of ammonia water to form metatitanic acid. Dissolve the metatitanic acid in lactate (85-90 wt %), which is as much as 7-10 times of the metatitanic acid. And then add water and heat up to 70° C. with water bath. When the mixture solution becomes clear from turbidity, the soluble titanium chelate is formed.

2. Add 300 mg of $KH_2PO_4$, 150 mg of $MgSO_4$, 7.5 mg of $FeCl_3.6H_2O$ and 1.5 mg of $CaCO_3$ into 150 mL of 2 mM/L $Ti(SO_4)_2$ solution. Well-mix and adjust pH to 7.0, then sterilize for 20 min at 121° C. After cooling, inoculate with 200 μl-500 μl of the above *Pseudomonas alcaliphila* MBR CGMCC2318 strain. And cultivate at 28-38° C. with shaking table at 110 rpm. After three to five days, centrifuge, and wash with deionized water (repeating 2-3 times), centrifuge again, then collect the precipitate. After freeze-drying, titanium oxide and elemental titanium among the precipitate is detected.

The reduction methods and steps of nonmetals silicon, selenium and tellurium are consistent with that mentioned above in the present invention. Their non-metal salts are used in the form of $Na_2SiO_3.9H_2O$, $Na_2SeO_3.5H_2O$ and $Na_2TeO_3$, respectively.

The elementary and ions state of metal and nonmetal oxide are detected by XPS (X-ray photoelectron spectroscopy) to calculate the contents of metal and nonmetal oxides and simple substances in the cell deposition by means of XPS characteristic peak area of elements in different valence states and of the sensitivity factor.

The result of XPS shows that *Pseudomonas alcaliphila* MBR CGMCC2318 can reduce metal ions in form of Fe(III), Pb(II), Co(II), Ni(II), Cu(II), Mn(II), Cd(II), Mo(VI), Ti(IV) in solution to elementary state, respectively. In addition, non-metal ions like Si(IV), Se(IV) and Te(IV) can also be reduced to elementary state.

The manipulation and analysis methods of adsorption of metal ions by *Pseudomonas alcaliphila* MBR CGMCC2318 of the present invention are shown as follow:

Firstly, the method and procedures of the strain activation are consistent with those of reduction of metal ions mentioned before.

Secondly, formulate 150 ml of NCTS culture medium and fill into 250 ml triangular flasks. Stopple flasks with cotton plugs, then autoclave at 121° C. After medium cools, inoculate with 50-200 μl of recent incubated *Pseudomonas alcaliphila* MBR CGMCC2318, then add 20-450 mg/L metal ion solution separately. The cultivation maintain for 3-5 days at constant temperature 28-38° C. and at 50-150 rpm shaking culture. Then collect cell pellet precipitation through centrifugation and wash 2-3 times with distilled water. After centrifugation, the cells are dried to constant weight and the supernatant fluid is used for detecting the concentration of residue metallic ions by inductively coupled plasma atomic emission spectrometry (ICP-AES). Then calculate the adsorbed metal quantity by means of the reduction of ion concentration and convert to the adsorption capacity per 1 g of dry cell.

Adsorption capacity(mg metal/g dry cell)=volume of solution×(initial concentration−final concentration)/dry cell In which:

Dry biomass: the difference between M and N(M-N), expressed by g, in which M means mixed dry weight of the bacteria and ions obtained from getting *Pseudomonas alcaliphila* MBR CGMCC2318 adsorb metal and then being dried for 2 h at 105° C., and N means the dry weight obtained from calcining the above-mentioned mixed dry weight for 2 h in muffle furnace at 500-600° C. and then weighing;

Initial concentration: the concentration of metal ions in the metal ion solution before adsorbing, expressed by mg/L.

Final concentration: the concentration of metal ions in the metal ion solution after adsorbing, expressed by mg/L.

Volume of solution: expressed by L.

The metal ions that can be adsorbed by *Pseudomonas alcaliphila* MBR CGMCC2318 of the present invention include Cu(II), Zn(II), Ni(II), Cd(II), Fe(III), Mn(II), Co(II), Pb(II), Al(III), whose adsorption methods and processes are same as the above. Among the detection methods of concentration of metal ions adsorbed by *Pseudomonas alcaliphila* MBR CGMCC2318 strain in the metal ion solution, dimethylglyoxime spectrophotometry is used for nickel(II) concentration detection, periodate oxidation spectrophotometry is used for manganese(II) concentration detection, X-ray photoelectron spectroscopy(XPS) is used for other metal ions concentration.

The concentration of metal ions has a significant impact on absorbability of the cell. For example, the bacteria have a good adsorption effect when nickel (II) concentration is lower than 5 mM, while more than 5 mM of nickel (II) concentration may do harm to cells and affect cell's growth.

The metal ions adsorption can be implemented through different inject manners, taking Ni (II) as the example, the specific operation is as follows:

Activated strain is transferred to sterilized NCTS liquid medium. After shaking culture for 3 d at 28-38° C. with shaking table at 50-150 rpm, add different concentration of $NiCl_2.6H_2O$, then adsorb for 2 h, 24 h, 48 h and 72 h, separately. Then detect metal ions concentration by dimethylglyoxime spectrophotometry method. The results show that adsorption rate is 66%-81% after 2 h and adsorption rate rises up to 91%-96% after 24 h. The results are shown in Table 3.

TABLE 3

The impact of different adsorption time on adsorption of metal ions

| Initial concentration (mg/L) | Final concentration of metal ions(mg/L)/ adsorption rate(%) | | | |
|---|---|---|---|---|
| | 2 h | 24 h | 48 h | 72 h |
| 115.6 | 38.9/66 | 10.37/91 | 11.4/90 | 2.92/97 |
| 174.8 | 33.7/81 | 8.8/95 | 10.89/94 | 5.8/97 |
| 231.8 | 44.6/81 | 10.37/96 | 12.96/94 | 7.79/97 |

Because adsorption can be carried out by live cell under aerobic condition, i.e. live cell adsorption, it can execute continuous adsorption by adding continuously metal ions into the above-mentioned culture solution in the present invention.

The present invention also relates to the application of the described strain *Pseudomonas alcaliphila* MBR CGMCC No. 2318 in bio-metallurgy, production of metal and nonmetal elementary substance, treatment of wastewater containing metal ions, and removal of harmful metal and nonmetal ions contained in the soil and stream.

Beneficial Effects

The Advantages of the Present Invention Consist in:

1. So far, electrode reaction phenomenon of reducing such low electrode potential metal elements by microbes has not yet reported in the publications, because the electrode potentials of reduced to their elementary state of some metallic ions, which include Fe(III), Mn(II), Cu(II), Ni(II), Cd(II), Co(II), Mo(VI), Pb(II), Ti(IV), are very low. While *Pseudomonas alcaliphila* MBR CGMCC2318 of the present invention have the ability of reducing directly metal ions in solutions, such as Fe(III), Mn(II), Cu(II), Ni(II), Cd(II), Co(II), Mo(VI), Pb(II), Ti(IV), to elementary state, which can cut down the cost greatly and recover metal resources.

2. So far, especially in respect of bio-reduction of nonmetallic silicon, there is not any relevant report abroad or domestically. It will be profoundly significant to produce silicon by the approach of bio-reduction and use the silicon in the fields of semiconductor, photoelectric materials and food additive etc.

3. Another prominent advantage of this invention is that the process of the said strain reducing metal ions is implemented under aerobic conditions, which means the condition is easy to control. Whereas in the public literature, most of the reduction from high oxidation state to low have been found carried out under strictly anaerobic conditions.

4. The *Pseudomonas alcaliphila* MBR CGMCC2318 of the present invention adsorb metal ions under aerobic conditions using live cells and have an increased adsorption capacity than dead cells do; moreover, it can be recycled and decrease processing cost significantly.

This invention applies to the treatment of wastewater (including electroplating wastewater, metal smelting, metal processing, etc.) and removal of harmful metal and nonmetal ions contained in the soil and stream.

BRIEF DESCRIPTION OF THE DRAWINGS

On Jan. 2, 2008, the strain *Pseudomonas alcaliphila* MBR has been preserved in China General Microbiological Culture Collection Center (CGMCC) of China Committee For Culture Collection of Microorganisms (CCCCM) whose address is Datun Road, Chaoyang District, Beijing, and the Collection No. is CGMCC No. 2318.

EMBODIMENTS

Example 1

The Culture of Strain *Pseudomonas alcaliphila* MBR CGMCC2318

1. Bacterial strain: *Pseudomonas alcaliphila* MBR CGMCC2318

2. Medium(NCTS) consists of: 1.0 g of $KNO_3$, 1.0 g of $KH_2PO_4$, 1.0 g of $MgSO_4.7H_2O$, 0.05 g of $FeCl_3.6H_2O$, 0.2 g of $CaCl_2.2H_2O$, 5.13 g of sodium citrate tribasic dehydrate, 1000 ml of distilled water.

3. Shaking culture:

Two loops of strain MBR from slant preservation inoculate in sterilized 100 ml LB culture medium and maintain for three days at 28° C. and 110 rpm shaking culture to achieve activation of strain. By the volume of NCTS liquid medium, then transfer 0.2% of inoculum to NCTS liquid medium and incubate for 48 h at 28° C. Repeat the above operation twice. Then the strain of *Pseudomonas alcaliphila* MBR CGMCC2318 is obtained.

Example 2

Properties of Reduction of Nitrate to Ammonia by *Pseudomonas alcaliphila* MBR CGMCC2318

Inoculate from plate colony to NCTS liquid medium with the sodium citrate as carbon sources. After culturing for 48 h at 28° C., detect ammonia nitrogen by Nesster's reagent colorimetric method; nitrite nitrogen detected by N-(1-naphthyl)-ethylenediamine colorimetric method, nitrate nitrogen detected by UV spectrophotometry. Aerobic and anaerobic experiments were carried out separately. The results proved that the growth rate of strain and reduction rate of nitrate under aerobic condition have more advantages than those under anaerobic condition. The nitrate can be reduced completely by the strain under aerobic condition and the ammonia accumulates to 28.2%. The results are shown in Table 4.

TABLE 4

The results of growth and ammonia production of *Pseudomonas alcaliphila* MBR CGMCC2318 at 72 h under aerobic and anaerobic conditions

| Culture condition | $OD_{600}$ | $NO_3^-$—N (%) | $NO_2^-$—N (%) | $NH_4^+$—N (%) [a] |
|---|---|---|---|---|
| Aerobic | 1.208 | 0 | 8.27 | 28.2 |
| anaerobic | 0.037 | 10.80 | 85.33 | 1.39 |

[a] the conversion rate of $NH_4^+$—N only comprises the part of soluble ammonia nitrogen reduced from nitrate in the solution.

Example 3

Reduction of Fe(III)

Formulate 100 ml NCTS medium according to the process in Example 1 and pour into a 250 ml flask, then stopple with cotton plug. Sterilize at 121° C., and after cooling, inoculate 200 μl of strain *Pseudomonas alcaliphila* MBR, CGMCC2318, then add metal salt $FeCl_3.6H_2O$ to 2 mM. Cultivate for five days at constant temperature 28° C. and at 110 rpm shaking culture, then allow to stand, strain appears to be flocculent precipitate. Centrifuge the precipitate and wash with deionized water (repeating 2-3 times). After freeze-dried, analyze the sample by X-ray Photoelectron Spectroscopy (XPS). The result of analysis shows that in the precipitate, by the total weight of iron, the weight of Fe (III) is 50.15 wt % and the weight of Fe (0) is 49.85 wt %, which means almost half of Fe (III) has been reduced to elementary substance.

Example 4

Reduction of Mn (II)

Figure 1:
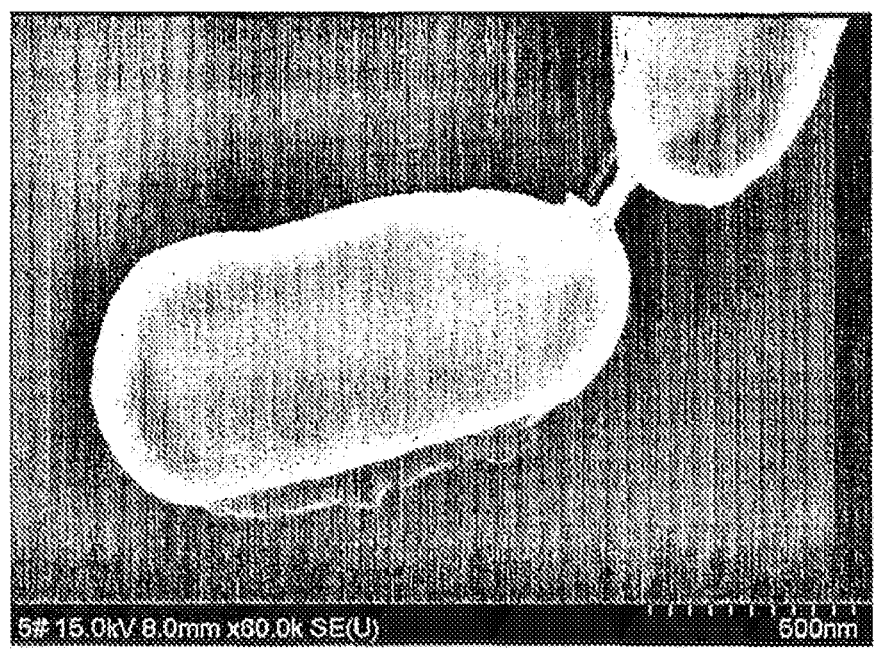
FIG. 1 shows the SEM image of *Pseudomonas alcaliphila* MBR.CGMCC2318.
Figure 2:
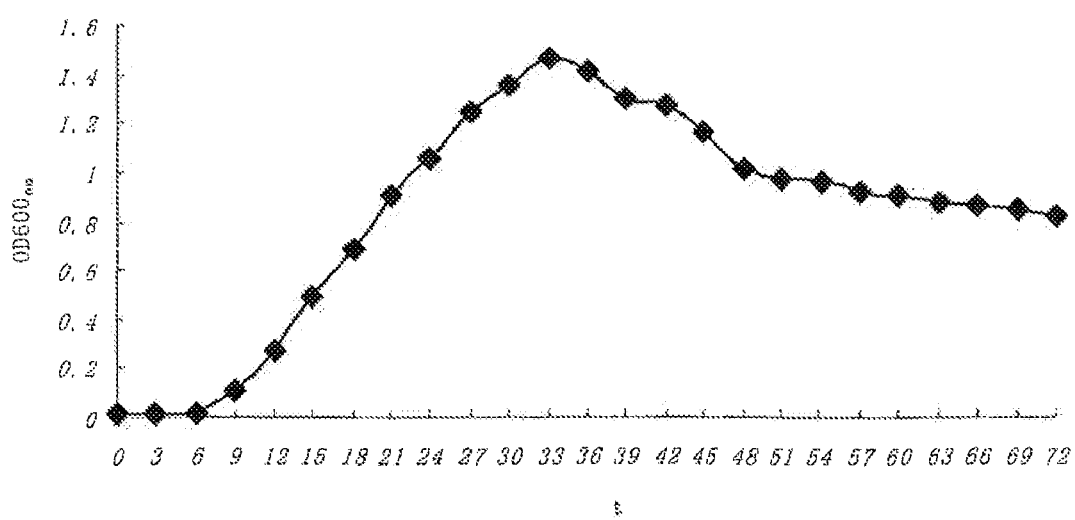
FIG. 2 shows the growth curve of *Pseudomonas alcaliphila* MBR.CGMCC2318.
Figure 3:
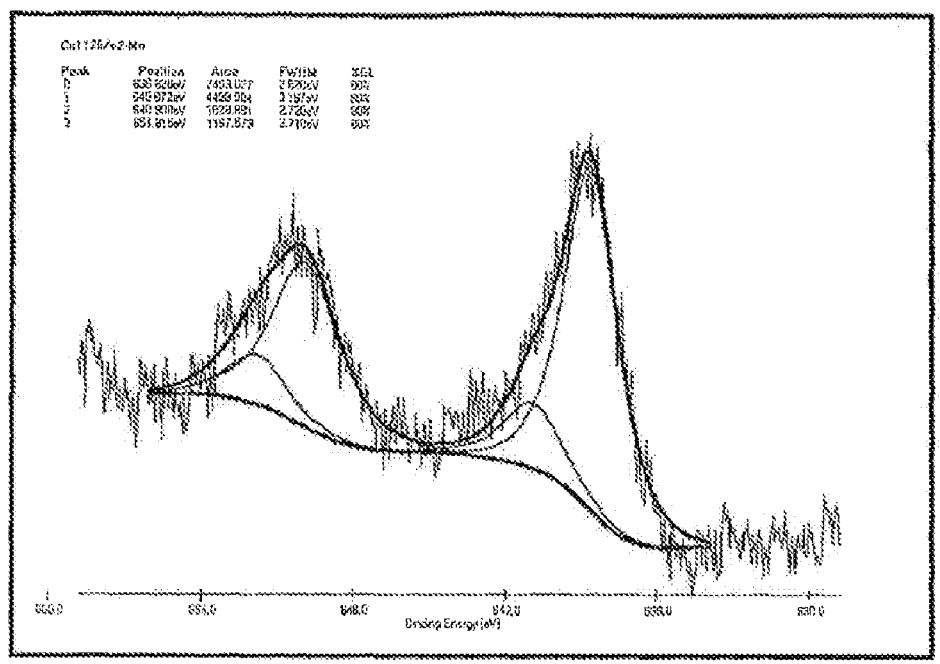
FIG. 3 shows the XPS spectra of reduction of Mn(II) by *Pseudomonas alcaliphila* MBR.CGMCC2318.
Figure 4:
FIG. 4 shows the TEM image of reduction of Mn(II) by *Pseudomonas alcaliphila* MBR.CGMCC2318.

Implementation procedures are the same as those of Example 3 except that the metal salt is 2 mM of $MnSO_4.H_2O$. The result of XPS spectra is shown as FIG. 3. The result shows that in the precipitate, by the total weight of manganese, the weight of Mn(II) is 17.12 wt % and the weight of Mn(0) is 82.88 wt %, which means 82.88 wt % of Mn(II) has been reduced to elemental manganese. The TEM image of the precipitate is shown as FIG. 4.

Example 5

Reduction of Cu (II)

Figure 5:
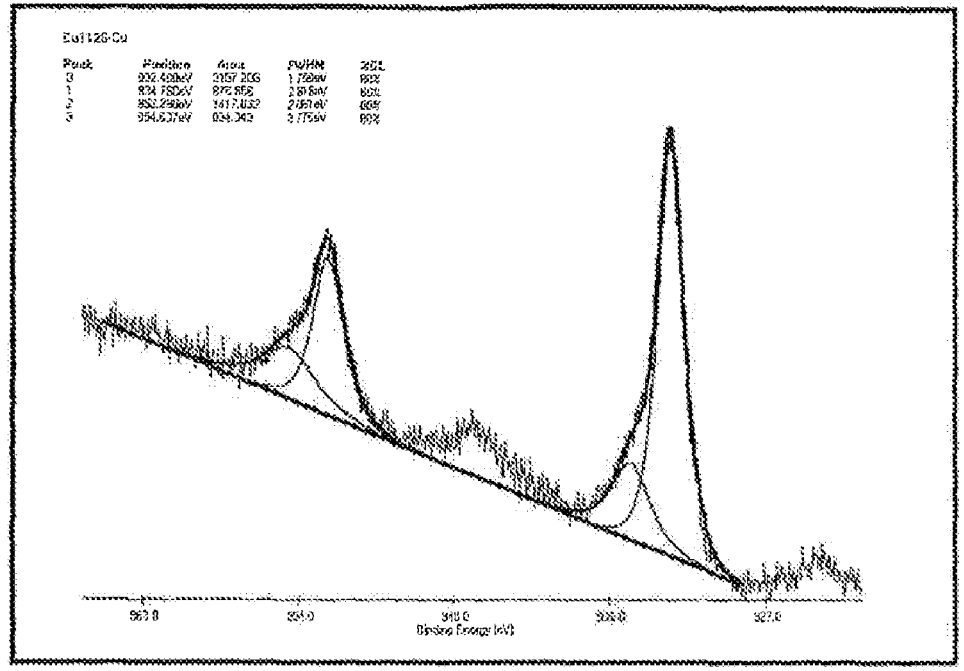
FIG. 5 shows the XPS spectra of reduction of Cu(II) by *Pseudomonas alcaliphila* MBR.CGMCC2318.

Implementation procedures are the same as those of Example 3 except that the metal salt is 2 mM of $CuSO_4.5H_2O$. The result of XPS spectra is shown as FIG. 5. The result shows that in the precipitate, by the total weight of copper, the weight of Cu(II) is 21.73 wt % and the weight of Cu(0) is 78.27 wt %, which means 78.27% of Cu (II) has been reduced to elemental copper.

Example 6

Reduction of Ni (II)

Implementation procedures are the same as those of Example 3 except that the metal salt is 2 mM of $NiCl_2.6H_2O$. The result of XPS spectra shows that in the precipitate, by the total weight of nickel, the weight of Ni (II) is 25.02 wt % and the weight of Ni (0) is 74.98 wt %, which means 74.98% of Ni(II) has been reduced to elemental nickel.

Example 7

Reduction of Cd(II)

Figure 6:
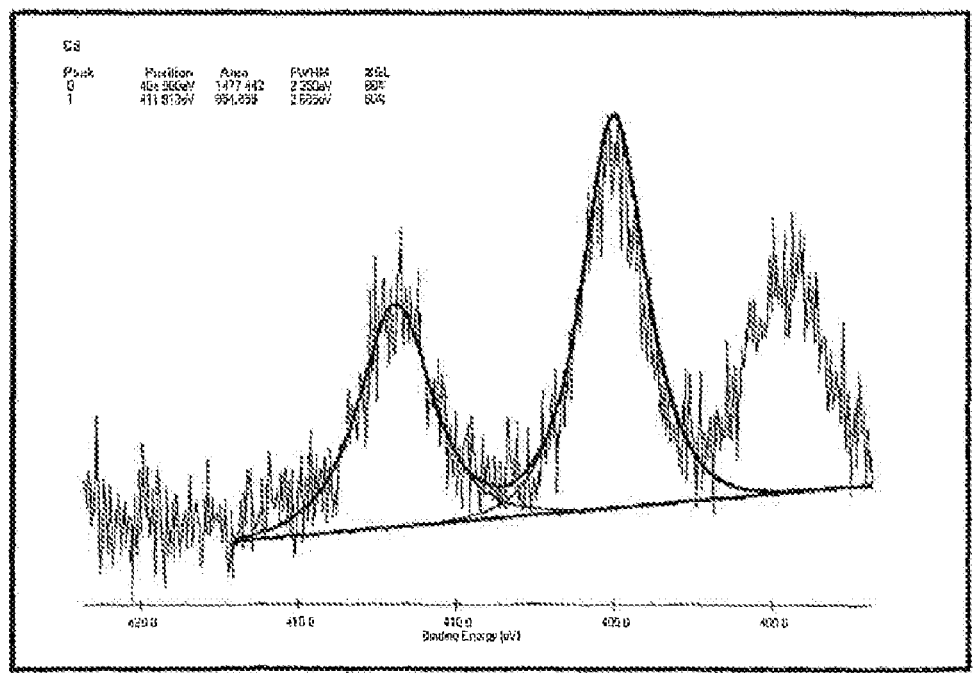
FIG. 6 shows the XPS spectra of reduction of Cd(II) by *Pseudomonas alcaliphila* MBR.CGMCC2318.

Implementation procedures are the same as those of Example 3 except that the metal salt is 1 mM of $3CdSO_4.8H_2O$. The result of XPS spectra is shown as FIG. 6. The result shows that in the precipitate, by the total weight of cadmium, the weight of Cd(II) is 0 and the weight of Cd(0) is 100 wt %, which means Cd(II) has been completely reduced to elemental cadmium.

Example 8

Reduction of Co(II)

Implementation procedures are the same as those of Example 3 except that the metal salt is 2 mM of $CoCl_2.6H_2O$. The result of XPS spectra shows that in the precipitate, by the total weight of cobalt, the weight of Co (II) is 40.96 wt % and the weight of Co (0) is 59.04%, which means 59.04% of Co(II) has been reduced to elemental cobalt.

Example 9

Reduction of Mo(VI)

Implementation procedures are the same as those of Example 3 except that the metal salt is 2 mM of $Na_2MoO_4.2H_2O$. The result of XPS spectra shows that in the precipitate, by the total weight of molybdenum, the weight of Mo (VI) is 63.08 wt % and the weight of Mo (0) is 36.92 wt %, which means 36.92% of Mo(VI) has been reduced to elemental molybdenum.

Example 10

Reduction of Pb(II)

Implementation procedures are the same as those of Example 3 except that the metal salt is 2 mM of $Pb(NO_3)_2$. The result of XPS spectra shows that in the precipitate, by the total weight of plumbum, the weight of Pb (II) is 76.92 wt % and the weight of Pb(0) is 23.08 wt %, which means 23.08% of Pb (II) has been reduced to elemental plumbum.

Example 11

Reduction of Titanium(IV)

1. Add a 0.5 ml of 15-18% $Ti(SO_4)_2$ solution into a 150 ml flask, then 1.7 ml of 25-28% ammonia, 4.0 ml-85-90% of lactate, and approximate 150 ml water, successively. Gradually heat the mixture with water bath to 70° C. As soon as turbidity becomes clear, a solution of 2 mM $Ti(SO_4)_2$ is formed.

2. Add 300 mg of $KH_2PO_4$, 150 mg of $MgSO_4$, 7.5 mg of $FeCl_3.6H_2O$ and 1.5 mg of $CaCO_3$ into 150 ml of 2 mM of $Ti(SO_4)_2$ solution prepared in step 1 and mix well. The mixture is adjusted to pH 7.0, stoppled with cotton plug and autoclaved for 20 min at 121° C. After cooling, inoculate 200 μl of inoculums of *Pseudomonas alcaliphila* MBR CGMCC2318 recently cultured in the Example 1. The cultivation maintain for five days at 28° C. and at 110 rpm shaking culture. Then collect precipitation and centrifuge, wash with deionized water for two-three times. Centrifuge again, freeze-dry the precipitate thus obtained, and detect the valence of metal ions by XPS. The result of XPS spectra shows that in the precipitate, by the weight of titanium, the weight of Ti (IV) is 69.02 wt % and the weight of Ti(0) is 30.98 wt %, which means 30.98% of Ti (IV) has been reduced to the simple substance.

Example 12

Reduction of Se(IV)

Figure 7:
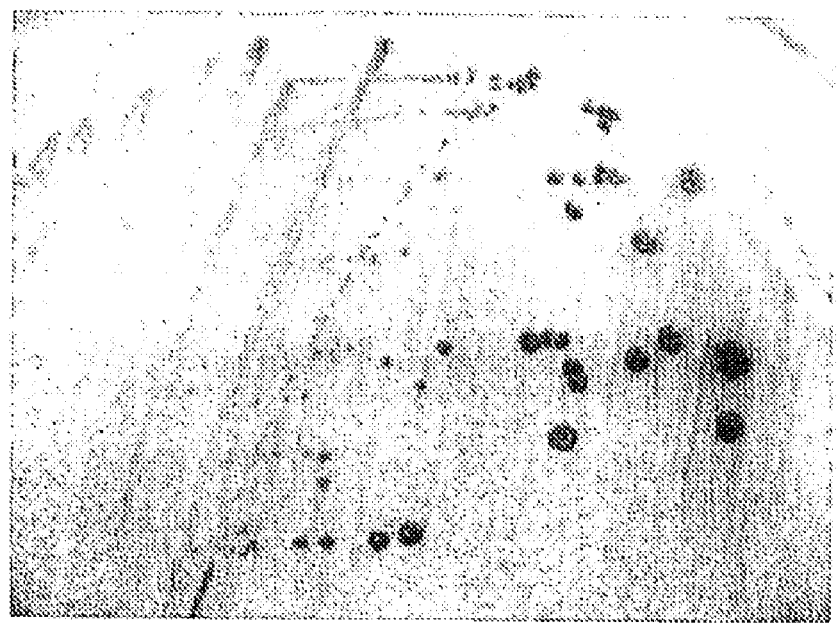
FIG. 7 shows colony image of the *Pseudomonas alcaliphila* MBR.CGMCC2318 grown on the petri plate with basal medium contained Se(IV)

The example has the same implementation procedures with Example 3, except that the non-metal ion is 2 mM of $Na_2SeO_3.5H_2O$. The cultivation maintain for two days at constant temperature 28° C. and at 110 rpm shaking culture, then the medium becomes red. After 5 days allow it stand, collect the precipitation and centrifuge, then wash with deionized water. Centrifuge again and obtain a kind of precipitation. The result of XPS spectra shows that in the precipitate, by the total weight of selenium, the weight of Se (IV) is 75.61 wt % and the weight of Se(0) is 24.39 wt %, that is to say part of Se (IV) has been reduced to Se(0). Growth of strain *Pseudomonas alcaliphila* MBR, CGMCC2318 grown on the solid medium containing Se(IV) is shown in FIG. 7.

Meanwhile, in the medium used in this example, decrease the weight of $MgSO_4.7H_2O$ from 1.0 g to 0.01 g, and supply with 0.99 g of potassium sulfate $K_2SO_4$ to eliminate the effect of sulfate ion, while keep other constituents and conditions unchanged. Operation is just the same as the above. The result shows that there is a prominent decrease in cell growth and a longer growth cycle when reducing the concentration of $Mg^{2+}$ in medium. Also, the result of XPS spectra shows that the reduction of Mg has little influence on reduction capacity of metals. In the precipitation, by the total weight of selenium, the weight of Se (IV) is 68.65 wt % and the weight of Se(0) is 22.16 wt %.

Example 13

Reduction of Te(IV)

Figure 8:
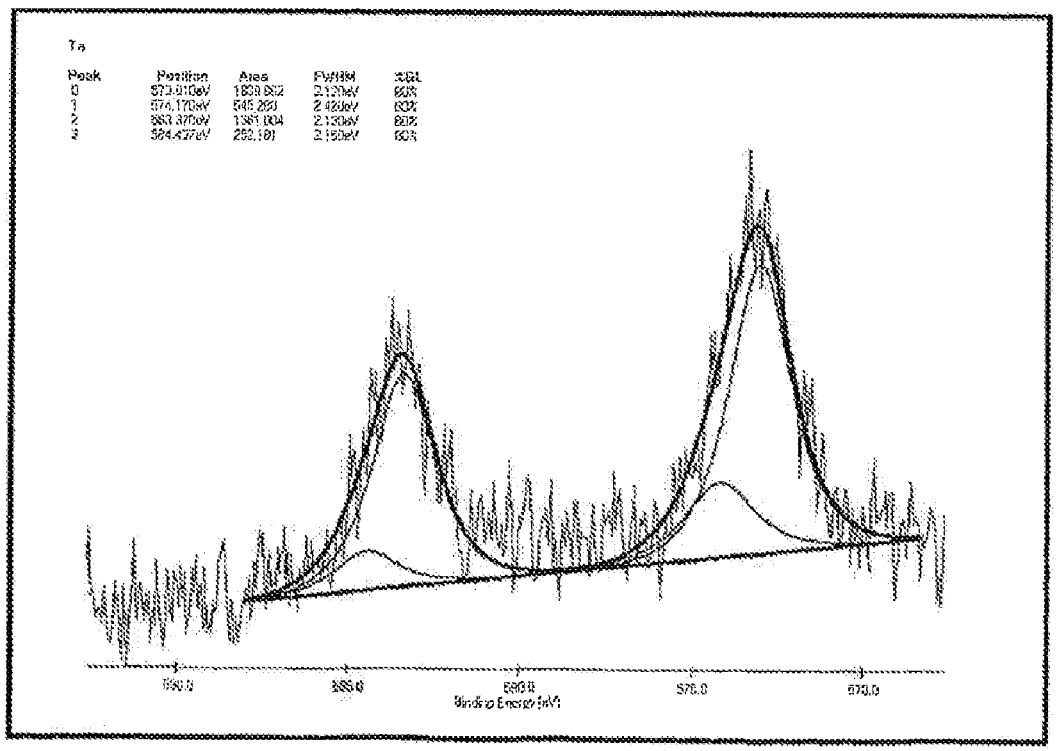
FIG. 8 shows the XPS spectra of reduction of Te(IV) by *Pseudomonas alcaliphila* MBR.CGMCC2318.

Implementation procedures are the same as those of Example 3 except that the nonmetal ion is 2 mM of $Na_2TeO_3$. The cultivation maintain for two days at constant temperature 28° C. and at 110 rpm shaking culture, then the medium becomes black. After 5 days, allow it stand and collect the precipitation, then centrifuge, wash with deionized water. Centrifuge again and obtain the precipitation. Centrifuge again, freeze-dry the precipitate thus obtained, and then execute XPS, whose result is shown as FIG. 8. The result shows that in the precipitation, by the total weight of tellurium, the weight of Te (IV) is 22.87 wt % and the weight of Te(0) is 77.13 wt %, which means most of the Te(IV) has been reduced to the simple substance Te(0).

Meanwhile, in the medium used in this example, decrease the weight of $MgSO_4.7H_2O$ from 1.0 g to 0.01 g, and supply with 0.99 g of potassium sulfate $K_2SO_4$ to eliminate the effect of sulfate ion, while keep other constituents and conditions unchanged. Operation is just the same as the above. The result shows that there is no growth after the first 4 days and appearance of dark in the solution at the fifth day, which means cell's growth cycle turns longer when reduce the concentration of $Mg^{2+}$ in medium. The result of XPS spectra also shows that the reduction of Mg in the medium has a prominent influence on reduction capacity of metals. In the precipitation, by the total weight of tellurium, the weight of Te (IV) is 68.65 wt % and the weight of Te(0) is only 31.35 wt %.

Example 14

Reduction of Si(IV)

Figure 9:
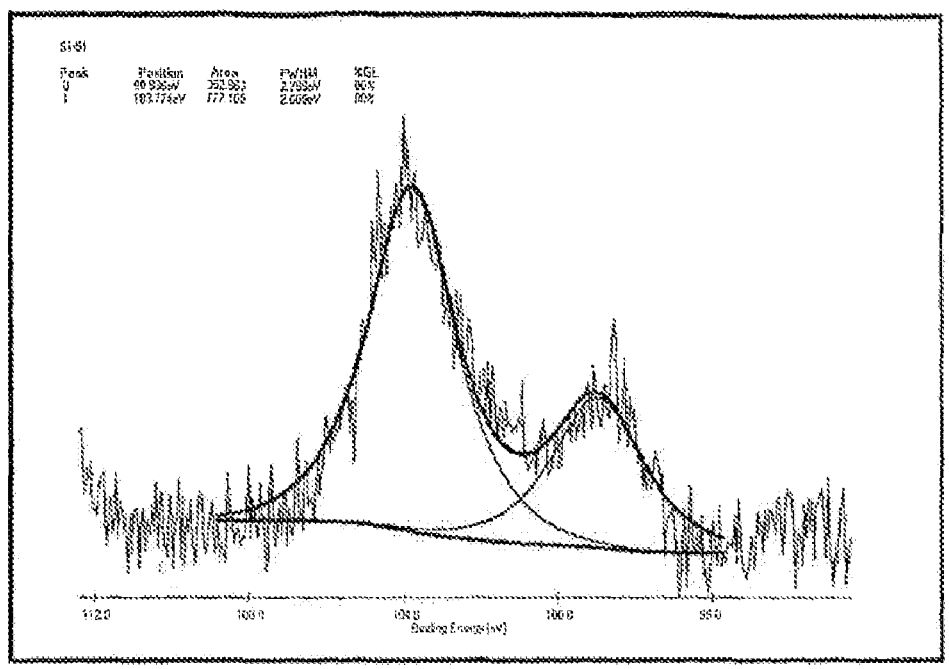
FIG. 9 shows the XPS spectra of reduction of Si(IV) by *Pseudomonas alcaliphila* MBR.CGMCC2318.
Figure 10:
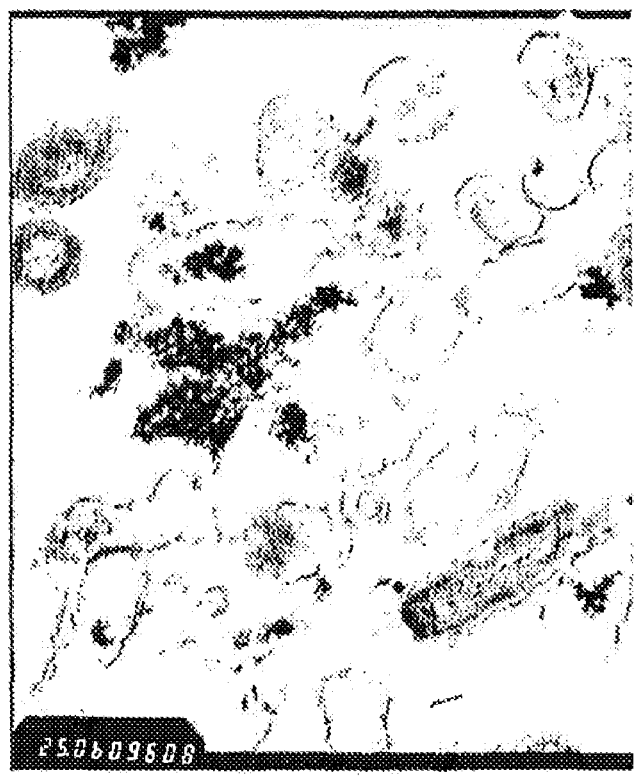
FIG. 10 shows the TEM image of reduction of Si(IV) by *Pseudomonas alcaliphila* MBR.CGMCC2318.

1. Into a 250 ml triangular flask, add 100 ml of medium formulated in Example 1, then stopple with cotton plug. Sterilize at 121° C., and after cooling, inoculate 200 µl of strain *Pseudomonas alcaliphila* MBR, CGMCC2318, then add 5 mM of $Na_2SiO_3.9H_2O$. Cultivate for five days at constant temperature 28° C. and at 110 rpm shaking culture. After 2 d, the culture solution turns cloudy. Allow to stand for 5 d, and then collect the precipitate and centrifuge. Wash with deionized water, centrifuge again to obtain the precipitate. After freeze-dried, the sample is analyzed by X-ray Photoelectron Spectroscopy (XPS), whose result is shown as FIG. 9. The result of analysis shows that in the precipitate, by the total weight of silicon, the weight of Si (IV) is 79.16 wt % and the weight of Si(0) is 20.84 wt %, which means part of silicon has been reduced to simple substance. The TEM image of the precipitate is shown as FIG. 10.

2. In the medium used in the above step, decrease the weight of $KH_2PO_4$ from 1.0 g to 0.1 g, add 1 mM of $Na_2SiO_3.9H_2O$, while other constituents and condition keep unchanged. The result shows that the reduction of P has no remarkable influence on cell growth. The result is shown as table 5.

TABLE 5

The effect of changes of reduction conditions on the results of reduction

| the conditions | Percentage (%) | |
|---|---|---|
| | Si(IV) | Si(0) |
| $Si^a$ | 79.16 | 20.84 |
| $Si^b$ | 68.76 | 31.24 |

$Si^a$: NCTS medium
$Si^b$: decrease $MgSO_4 \cdot 7H_2O$ from 1.0 g to 0.01 g in NCTS medium.

Example 15

Adsorption of Cu(II)

Add 150 ml of NCTS medium into a 250 ml triangular flask and stopple cotton plug. Sterilize at 121° C., and after cooling, inoculate 200 µl of strain *Pseudomonas alcaliphila* MBR, CGMCC2318 incubated in the Example 1. Then add 5 mM of $CuSO_4.5H_2O$ (initial concentration of copper ion is 294 mg/L). The cultivation maintain for 5 days at constant temperature 28° C. and at 110 rpm shaking culture. Then centrifuge the culture solution, obtain the precipitate, and wash 2-3 times with water. After centrifugation, dry and weigh, obtain supernatant liquid to detect the concentration of copper ion.

The result after adsorption of bacteria, initial decreases from 294 mg/L to 8.13 mg/L. Removal of copper ion is 285.87 mg/L. The total weight of 150 ml of culture solution and adsorbed copper is 0.169 g, the weight of adsorbed copper is 42.88 mg, and the cell itself weighs 0.126 g. That is to say, adsorption capacity of the described cell of the present invention adsorbing copper ion is 340 mg/g dry cell.

Example 16

Adsorption of Zn(II)

Methods and steps are the same with Example 15. Add 10 mM of $ZnSO_4.7H_2O$. After adsorption of bacteria, initial decreases from 424.5 mg/L to 0.332 mg/L. The total weight of 150 ml of culture solution and adsorbed zinc is 0.235 g, the weight of adsorbed zinc is 63.63 mg, and the cell itself weighs 0.17 g. That is to say, adsorption capacity of the described cell of the present invention adsorbing zinc ion is 372.35 mg/g dry cell.

Example 17

Adsorption of Ni(II)

Figure 11:
FIG. 11 shows the TEM image of adsorption of Ni(II) by *Pseudomonas alcaliphila* MBR.CGMCC2318.

Methods and steps are the same with Example 15. Add 3 mM of $NiCl_2.6H_2O$. After adsorption of bacteria, initial decreases from 161.4 mg/L to 6.415 mg/L. The total weight of 150 ml of culture solution and adsorbed nickel is 0.16 g, the weight of adsorbed nickel is 23.25 mg, and the cell itself weighs 0.137 g. That is to say, adsorption capacity of the described cell of the present invention adsorbing nickel ion is 169.75 mg/g dry cell. The TEM image of adsorption of Ni(II) by cell is shown in FIG. 11.

Example 18

Adsorption of Cd(II)

Methods and steps are the same with Example 15. Add 1 mM of $3CdSO_4.8H_2O$. After adsorption of bacteria, initial cadmium decreases from 111 mg/L to 1.14 mg/L. The total weight of 150 ml of culture solution and adsorbed cadmium is 0.147 g, the weight of absorbed cadmium is 16.48 mg and the cell itself weighs 0.131 g. That is to say, adsorption capacity of the described cell of the present invention adsorbing cadmium ion is 125.87 mg/g dry cell.

Example 19

Adsorption of Fe(III)

Methods and steps are the same with Example 15. Add 4 mM of $FeCl_3.6H_2O$. After adsorption of bacteria, initial decreases from 224 mg/L to 0.122 mg/L. The total weight of 150 ml of culture solution and adsorbed iron is 0.493 g and the weight of adsorbed iron is 33.58 mg, the cell itself weighs 0.46 g. That is to say, adsorption capacity of the described cell of the present invention adsorbing iron ion is 73.1 mg/g dry cell.

Example 20

Adsorption of Mn(II)

Methods and steps are the same with Example 15. Add 2 mM of $MnSO_4.H_2O$. After adsorption of bacteria, initial manganese ion decreases from 94.4 mg/L to 5.09 mg/L. The total weight of 150 ml of culture solution and adsorbed manganese is 0.09 g and the weight of adsorbed manganese is 13.4 mg, the cell itself weighs 0.075 g. That is to say, adsorption capacity of the described cell of the present invention adsorbing manganese ion is 178.85 mg/g dry cell.

Example 21

Adsorption of Co(II)

Methods and steps are the same with Example 15. Add 2 mM of $CoCl_2.6H_2O$. After adsorption of bacteria, initial decreases from 119 mg/L to 11.8 mg/L. The total weight of 150 ml of culture solution and adsorbed cobalt is 0.157 g and the weight of adsorbed cobalt is 16.08 mg, the cell itself weighs 0.14 g. That is to say, adsorption capacity of the described cell of the present invention adsorbing cobalt ion is 114.51 mg/g dry cell.

Example 22

Adsorption of Pb(II)

Methods and steps are the same with Example 15. Add 1 mM of $Pb(NO_3)_2$. After adsorption of bacteria, initial decreases from 186.78 mg/L to 0.418 mg/L. The total weight of 150 ml of culture solution and adsorbed plumbum is 0.183 g, and the weight of adsorbed plumbum is 27.95 mg, the cell itself weighs 0.155 g. That is to say, adsorption capacity of the described cell of the present invention adsorbing plumbum ion is 180.18 mg/g dry cell.

Example 23

Adsorption of Al(III)

Methods and steps are the same with Example 15. Add 1 mM of $Al_2(SO_4)_3$. After adsorption of bacteria, initial decreases from 92.8 mg/L to 3.28 mg/L. The total weight of 150 ml of culture solution and adsorbed aluminium is 0.123 g and the weight of adsorbed aluminium is 13.43 mg, the cell itself weighs 0.11 g. That is to say, adsorption capacity of the described cell of the present invention adsorbing aluminium ion is 122.1 mg/g dry cell.

Example 24

Taking Ni(II) as the Example, the Influence of Concentrations of Metal Ion on the Adsorption Capacity of *Pseudomonas alcaliphila* MBR CGMCC2318

The culture methods are the same with Example 1. 100 ml of NCTS medium are separately loaded in several 250 ml triangular flasks. Sterilize for 20 min at 121° C. After cooling, inoculate 200 µl *Pseudomonas alcaliphila* MBR CGMCC2318 recent cultured in Example 1. Then add $NiCl_2.6H_2O$ to make their initial concentrations of $Ni^{2+}$ separately are 0.5 mM, 1.0 mM, 2 mM, 5 mM and 7 mM. Subsequently, maintain at constant temperature 28° C. and shaking culture at 110 rpm with shaking table.

Figure 12:
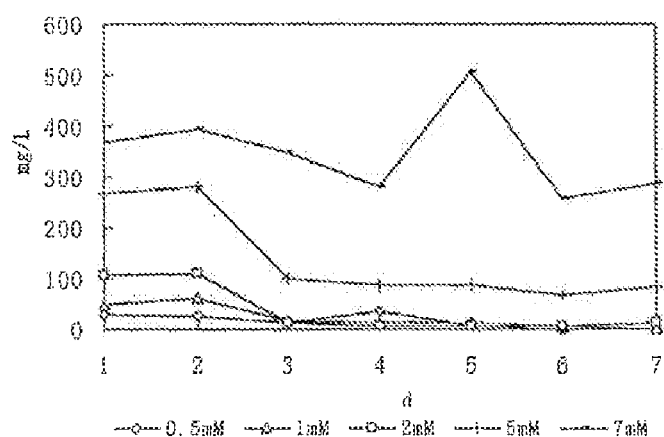
FIG. 12 shows the influence of different concentrations of Ni(II) on the adsorption capacity of cell.

Detect the concentration of $Ni^{2+}$ in solution by dimethylglyoxime spectrophotometric method everyday. The results prove that the concentration of $Ni^{2+}$ has no change at the first two days. However, the concentration of $Ni^{2+}$ in culture medium whose initial concentration is lower than 5 mM decrease quickly from the third day, while $Ni^{2+}$ in culture with more than 5 mM of initial concentration become poisonous to cell and concentration of $Ni^{2+}$ has no change. The results are shown as FIG. 12.

Example 25

Taking Mn(II) as the Example, the Influence of Concentrations of Metal Ion on the Adsorption Capacity of *Pseudomonas alcaliphila* MBR CGMCC2318

Figure 13:
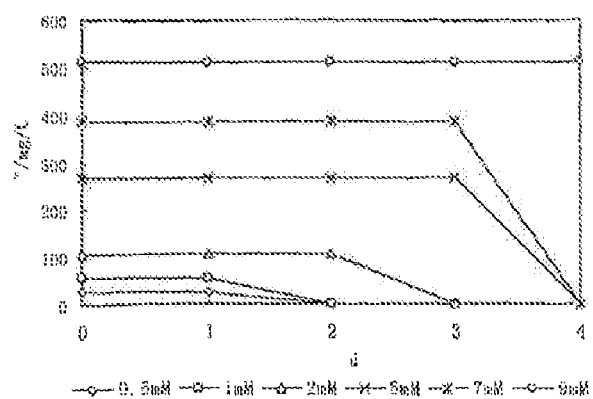
FIG. 13 shows the influence of different concentrations of Mn(II) on the adsorption capacity of cell.

Methods and steps are the same with Example 24. Detect the content of manganese by periodate oxidation spectrophotometric method. The results prove that the higher the concentration of manganese ion is, the longer the adsorption time needs. As shown in FIG. 13, the adsorption completely cannot be carried out when the concentration of manganese ion exceeds 7 mM.

The invention claimed is:

1. A strain *Pseudomonas alcaliphila* MBR, characterized by capability of growth at pH 6 to pH 9 and capability of nitrate reduction and having a 16S ribosomal RNA gene sequence of SEQ ID NO: 1.

2. A method of reduction or adsorption of metal ions comprising adding one or more metal salt(s) to a culture of *Pseudomonas alcaliphila* MBR characterized by capability of growth at pH 6 to pH 9 and capability of nitrate reduction and having a 16S ribosomal RNA gene sequence of SEQ ID NO: 1, incubating the culture, and recovering a precipitate comprising the reduced metal ions or adsorbed metal ions from the culture.

3. The method of claim 2, in which the metal salts are selected from the group consisting of one or more salt(s) of Fe(III), Mn(II), Cu(II), Ni(II), Cd(II), Co(II), Mo(VI), Pb(II) and Ti(IV).

4. The method of claim 3, in which the medium for culture of *Pseudomonas alcaliphila* MBR (strain CGMCC No. 2318) comprises 0.5-1.0 part of $KNO_3$, 0.1-1.0 part of $KH_2PO_4$, 0.01-1.0 part of $MgSO_4.7H_2O$, 0.05 part of $FeCl_3.6H_2O$, 0.2 part of $CaCl_2.2H_2O$ and 0.9-6.9 parts of sodium citrate in 1000 parts of distilled water.

5. The method of claim 3, in which the culture is maintained at 28-38° C. and pH 6.0-10.0 for 3-5 days.

6. The method of claim 4, in which the culture is maintained at 28-38° C. and pH 6.0-10.0 for 3-5 days.

7. The method of claim 3, in which the metal salt(s) are added as $FeCl_3.6H_2O$, $MnSO_4.H_2O$, $CuSO_4.5H_2O$, $NiCl_2.6H_2O$, $3CdSO_4.8H_2O$, $CoCl_2.6H_2O$, $Na_2MoO_4.2H_2O$ or $Pb(NO_3)_2$, respectively.

8. The method of claim 4, in which the metal salt(s) are added as $FeCl_3.6H_2O$, $MnSO_4.H_2O$, $CuSO_4.5H_2O$, $NiCl_2.6H_2O$, $3CdSO_4.8H_2O$, $CoCl_2.6H_2O$, $Na_2MoO_4.2H_2O$ or $Pb(NO_3)_2$, respectively.

9. The method of claim 5, in which the metal salt(s) are added as $FeCl_3.6H_2O$, $MnSO_4.H_2O$, $CuSO_4.5H_2O$, $NiCl_2.6H_2O$, $3CdSO_4.8H_2O$, $CoCl_2.6H_2O$, $Na_2MoO_4.2H_2O$ or $Pb(NO_3)_2$, respectively.

10. The method of claim 6, in which the metal salt(s) are added as $FeCl_3.6H_2O$, $MnSO_4.H_2O$, $CuSO_4.5H_2O$, $NiCl_2.6H_2O$, $3CdSO_4.8H_2O$, $CoCl_2.6H_2O$, $Na_2MoO_4.2H_2O$ or $Pb(NO_3)_2$, respectively.

11. The method of claim 2, in which a Ti(IV) salt is reduced from a soluble titanium chelate formed by dissolving metatitanic acid in lactate.

12. The method of claim 2, in which $TiSO_4$ is reduced and the culture medium comprises $KH_2PO_4$, $MgSO_4$, $FeCl_3.6H_2O$, $CaCO_3$ and $TiSO_4$.

13. The method of claim 2, in which one or more metal ions selected from the group consisting of Cu(II), Zn(II), Ni(II), Cd(II), Fe(II), Mn(II), Co(II), Pb(II) and Al(III) are adsorbed.

14. The method of claim 13, in which the culture medium comprises 0.5-1.0 part of $KNO_3$, 0.1-1.0 part of $KH_2PO_4$, 0.01-1.0 part of $MgSO_4.7H_2O$, 0.05 part of $FeCl_3.6H_2O$, 0.2 part of $CaCl_2.2H_2O$ and 0.9-69 parts of sodium citrate in 1000 parts of distilled water.

15. The method of claim 13, in which the culture time is 24 to 72 hours.

16. The method of claim 14, in which the culture time is 24 to 72 hours.

17. The method of claim 2, in which the precipitate is recovered by centrifugation of the culture and recovery of the cells.

18. The method of claim 2, in which the reduced metal ions or the adsorbed metal ions are recovered from the cells by calcining the precipitate at a temperature of from 500 to 600° C.

19. The method of claim 2, in which the strain of *Pseudomonas alcaliphila* MBR is the isolate deposited as CGMCC No. 2318.

20. The strain of *Pseudomonas alcaliphila* MBR of claim 1 that is the isolate deposited as CGMCC No. 2318.

* * * * *

SEQUENCE LISTING

<160> NUMBER OF SEQ ID NOS: 1

<210> SEQ ID NO 1
<211> LENGTH: 1328
<212> TYPE: DNA

```
<213> ORGANISM: Unknown
<220> FEATURE:
<223> OTHER INFORMATION: microorganism

<400> SEQUENCE: 1
tttagcggcg gaagggtgag taatgcctag gaatctgcct ggtagtgggg gataacgttc        60
cgaaaggaac gctaataccg catacgtcct acgggagaaa gcaggggacc ttcgggcctt       120
gcgctatcag atgagcctag gtcggattag ctagttggtg aggtaatggc tcaccaaggc       180
gacgatccgt aactggtctg agaggatgat cagtcacact ggaactgaga cacggtccag       240
actcctacgg gaggcagcag tggggaatat tggacaatgg gcgaaagcct gatccagcca       300
tgccgcgtgt gtgaagaagg tcttcggatt gtaaagcact taagttggg aggaagggca       360 ttaacctaat acgttagtgt tttgacgtta ccgacagaat aagcaccggc taacttcgtg       420
ccagcagccg cggtaatacg aagggtgcaa gcgttaatcg gaattactgg gcgtaaagcg       480
cgcgtaggtg gttcgttaag ttggatgtga agcccgggg ctcaacctgg gaactgcatc       540
caaaactggc gagctagagt acggtagagg gtggtggaat ttcctgtgta gcggtgaaat       600
gcgtagatat aggaaggaac accagtggcg aaggcgacca cctggactga tactgacact       660
gaggtgcgaa agcgtgggga gcaaacagga ttagataccc tggtagtcca cgccgtaaac       720
gatgtcaact agccgttggg ttccttgaga acttagtggc gcagctaacg cattaagttg       780
accgcctggg gagtacggcc gcaaggttaa aactcaaatg aattgacggg ggcccgcaca       840
agcggtggag catgtggttt aattcgaagc aacgcgaaga accttacctg gccttgacat       900
gctgagaact ttccagagat ggattggtgc cttcgggagc tcagacacag gtgctgcatg       960
gctgtcgtca gctcgtgtcg tgagatgttg ggttaagtcc cgtaacgagc gcaacccttg      1020
tccttagtta ccagcacgta atggtgggca ctctaaggag actgccggtg acaaaccgga      1080
ggaaggtggg gatgacgtca agtcatcatg gcccttacgg ccagggctac acacgtgcta      1140
caatggtcgg tacaaagggt tgccaagccg cgaggtggag ctaatcccat aaaaccgatc      1200
gtagtccgga tcgcagtctg caactcgact gcgtgaagtc ggaatcgcta gtaatcgtga      1260
atcagaatgt cacggtgaat acgttcccgg gccttgtaca caccgcccgt caccccatgg      1320
gtgtgggt                                                               1328
```